United States Patent
Miyake et al.

(12) United States Patent (10) Patent No.: US 7,553,274 B2
Miyake et al. (45) Date of Patent: Jun. 30, 2009

(54) CAPSULE ENDOSCOPE

(75) Inventors: Kiyoshi Miyake, Asaka (JP); Mitsuo Obata, Tokyo (JP)

(73) Assignee: Olympus Corporation (JP)

( * ) Notice: Subject to any disclaimer, the term of this patent is extended or adjusted under 35 U.S.C. 154(b) by 108 days.

(21) Appl. No.: 10/859,824

(22) Filed: Jun. 3, 2004

(65) Prior Publication Data
US 2005/0020880 A1 Jan. 27, 2005

(30) Foreign Application Priority Data
Jun. 4, 2003 (JP) ............................. 2003-159959

(51) Int. Cl.
*A61B 1/00* (2006.01)
(52) U.S. Cl. ..................... 600/121; 600/101; 600/122; 600/123; 600/124; 600/125
(58) Field of Classification Search ............... 600/101, 600/109, 114, 115, 121, 127, 129, 134, 102, 600/160
See application file for complete search history.

(56) References Cited
U.S. PATENT DOCUMENTS
5,415,157 A * 5/1995 Welcome .................... 600/121
6,369,706 B1 * 4/2002 Anderson et al. ............ 340/521
2002/0103417 A1 * 8/2002 Gazdzinski ................. 600/109
2003/0060734 A1 * 3/2003 Yokoi et al. ................. 600/593
2003/0171652 A1 * 9/2003 Yokoi et al. ................. 600/160
2004/0106849 A1 * 6/2004 Cho et al. .................... 600/101

FOREIGN PATENT DOCUMENTS
JP 2001-091860 4/2001

\* cited by examiner

*Primary Examiner*—Linda C Dvorak
*Assistant Examiner*—Matthew J Kasztejna
(74) *Attorney, Agent, or Firm*—Ostrolenk, Faber, LLP

(57) ABSTRACT

A protective body packages an exterior of a capsule endoscope body of a capsule endoscope such that a field of vision of an objective lens system is not obstructed. As a result, even if the capsule endoscope collides against a wall surface inside an object being examined, a circular cylinder portion of the protective body is elastically deformed so that the protective body itself becomes a shock absorbing portion and protects each portion inside a case as well as actual LED covers and a lens cover. As a result, the capsule endoscope body can be recovered in an undamaged condition, and unnecessary costs can be reduced by reusing the capsule endoscope body.

5 Claims, 18 Drawing Sheets

CAPSULE ENDOSCOPE

BACKGROUND OF THE INVENTION

1. Field of the Invention

The present invention relates to a capsule endoscope that is provided with a protective function against surrounding objects and impacts.

Priority is claimed on Japanese Patent Application No. 2003-159959, filed Jun. 4, 2003, the contents of which are incorporated herein by reference.

2. Description of Related Art

In recent years, an endoscope that is configured as a capsule in which an observation optical section, an illumination section, an image pickup section, and a transceiver and the like are incorporated in a single body, and that is known as a capsule endoscope has been developed. When this capsule endoscope is used in the field of medicine in an internal examination of a patient, it is swallowed like a tablet, while when it is used in the field of industry in an internal inspection of a pipe or the like, it is inserted into the interior of the pipe. Consequently, an observed image of an object that is taken by the observation section in the capsule endoscope can be displayed on the screen of an external observation apparatus.

In Japanese Unexamined Patent Application, First Publication No. 2001-91860, for example, a capsule endoscope is disclosed in which the internal instruments are placed in an airtight state using a packaging case that includes a substantially semispherical transparent cover and a cylindrical cover whose rear end portion has a semispherical configuration, and an observation image is obtained by focusing an object that is illuminated using a light emitting diode on an image sensor using an objective lens system.

SUMMARY OF THE INVENTION

The present invention is a capsule endoscope that is inserted into an object being examined and makes an observation of an interior of the object being examined comprising:
a capsule endoscope body; and a protective body that is provided on an exterior of the capsule endoscope body without obstructing a field of vision of the capsule endoscope body, and that protects the capsule endoscope body from shocks caused by collisions with surrounding objects.

The present invention is a capsule endoscope that is inserted into an object being examined and makes an observation of an interior of the object being examined comprising:
an observation device that observes the interior of the object being examined; and a protective body that protects the observation device.

It is preferable that the protective body is provided that protects the observation device by absorbing shock.

It is preferable that the protective body is provided that the observation device by absorbing shock as a result of the protective body being able to deform freely.

It is preferable that the protective body is formed by an elastic body.

It is preferable that the protective body is formed by a solid body that is freely plastically deformable.

The present invention is a capsule endoscope that is inserted into an object being examined and makes an observation of an interior of the object being examined comprising:
an observation device that observes the interior of the object being examined; a capsule endoscope body that has the observation device; and a protective body that protects the capsule endoscope body.

It is preferable that wherein, the protective body is formed by an elastic body.

It is preferable that the protective body is formed by a solid body that is freely plastically deformable.

It is preferable that the protective body provides on an outer packaging body that constitutes an outer package of the capsule endoscope body.

It is preferable that the protective body provides on an outer packaging body that constitutes an outer package of a capsule endoscope body, and the protective body holds as a portion of the outer packaging body.

It is preferable that the protective body is bag shaped.

It is preferable that a combination of the protective body and the outer packaging body is formed by pressure insertion.

It is preferable that the protective body covers the outer packaging body; and the protective body and the outer packaging body are fastened by binding end portions of the bag shape.

BRIEF DESCRIPTION THE DRAWINGS

DETAILED DESCRIPTION OF THE INVENTION

Figure 1:
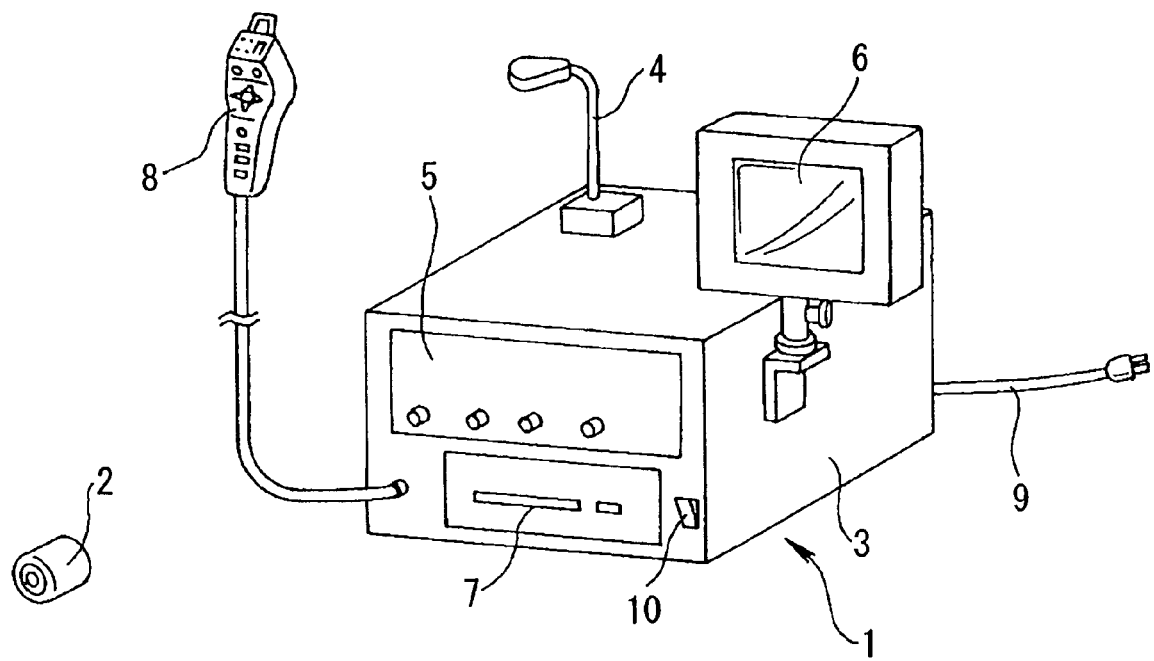
FIG. 1 is a structural view of a capsule endoscope apparatus according to a first embodiment of the present invention.
Figure 2:
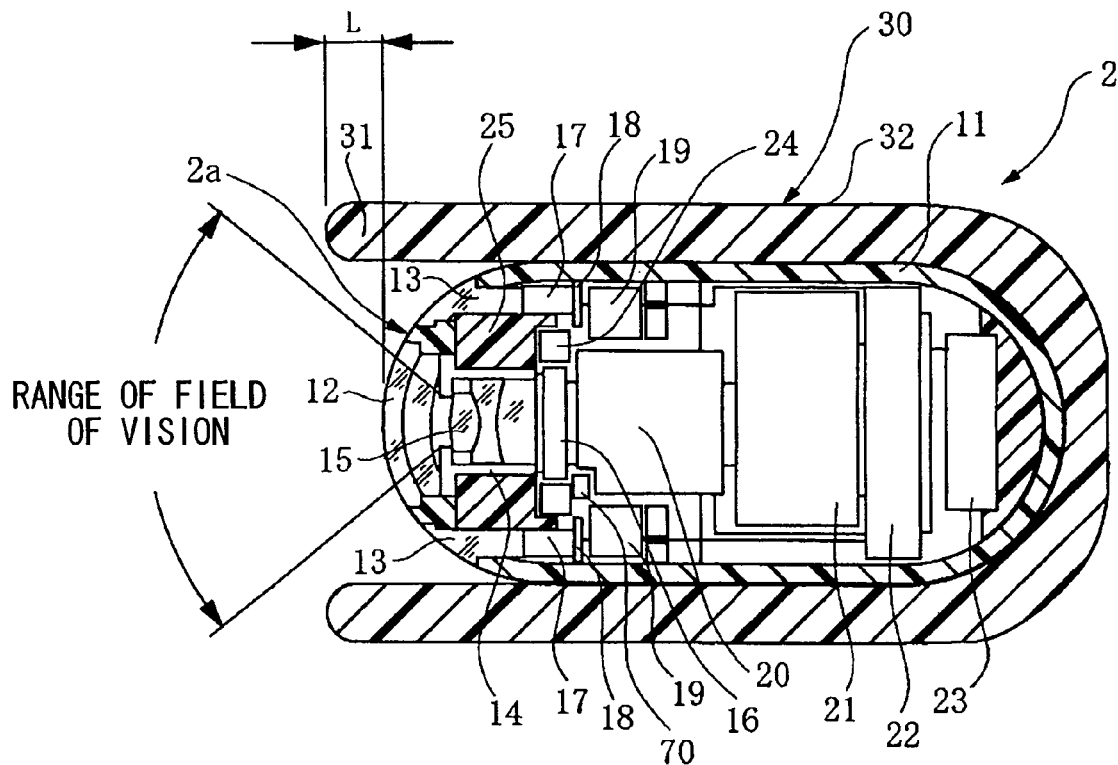
FIG. 2 is a structural view of the capsule endoscope according to a first embodiment of the present invention.
Figure 3:
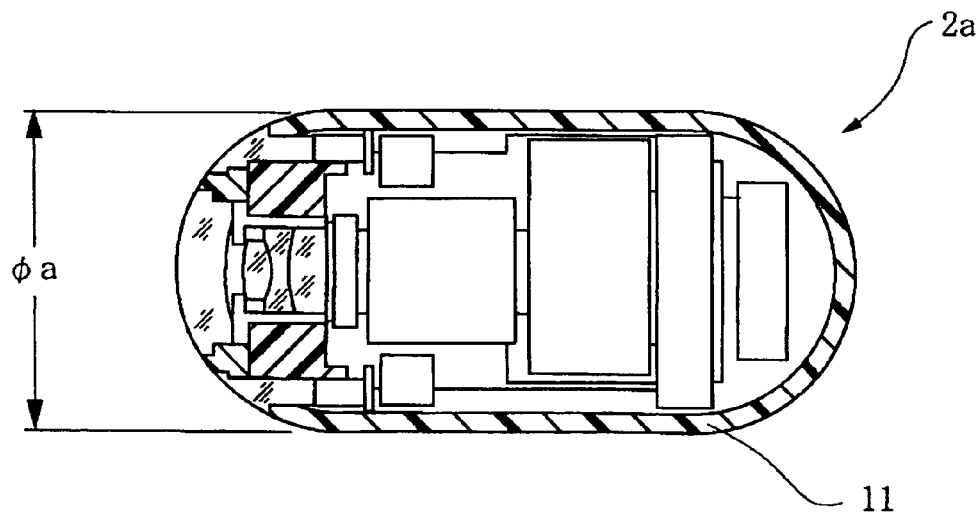
FIG. 3 is an explanatory view showing an outer diameter of the capsule endoscope according to a first embodiment of the present invention.
Figure 4:
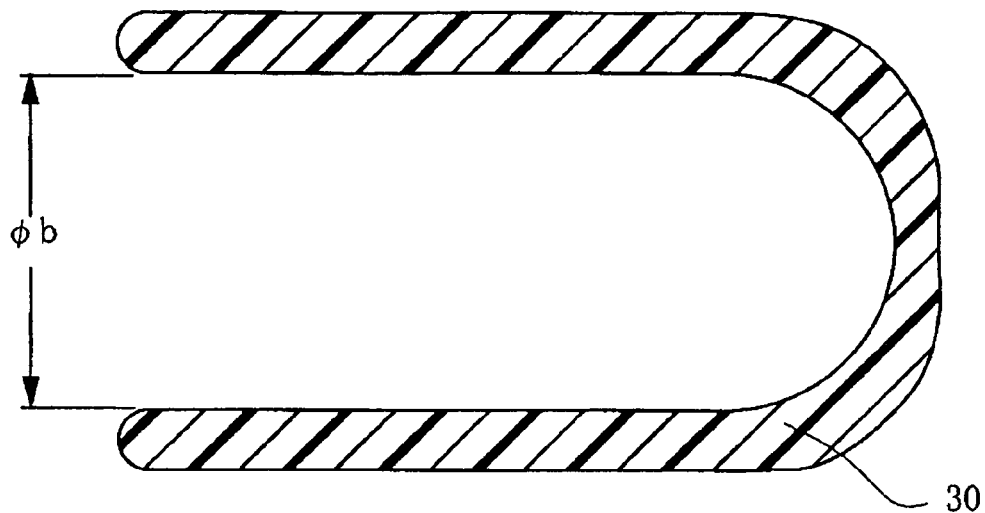
FIG. 4 is an explanatory view showing an inner diameter of a protective body according to a first embodiment of the present invention.
Figure 5:
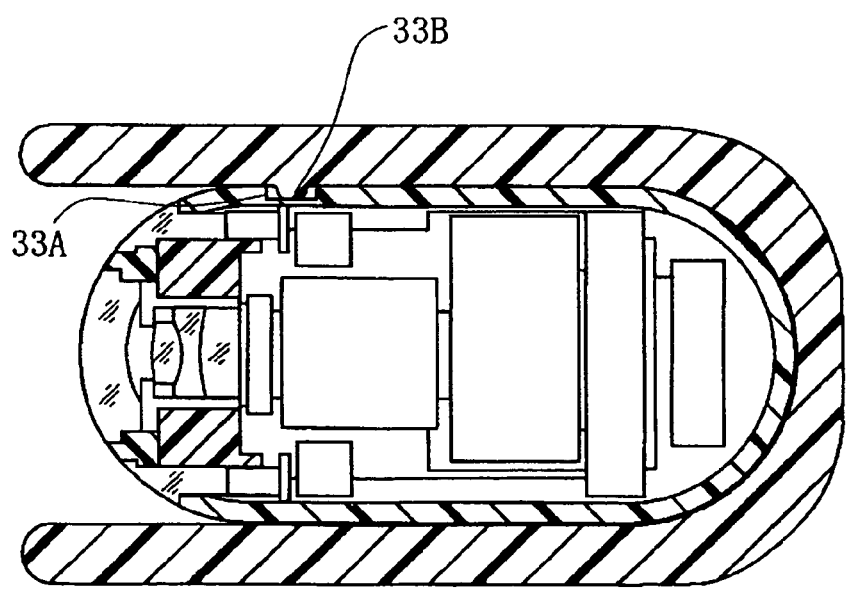
FIG. 5 is an explanatory view showing another example of a mounting of the protective body according to a first embodiment of the present invention.
Figure 6:
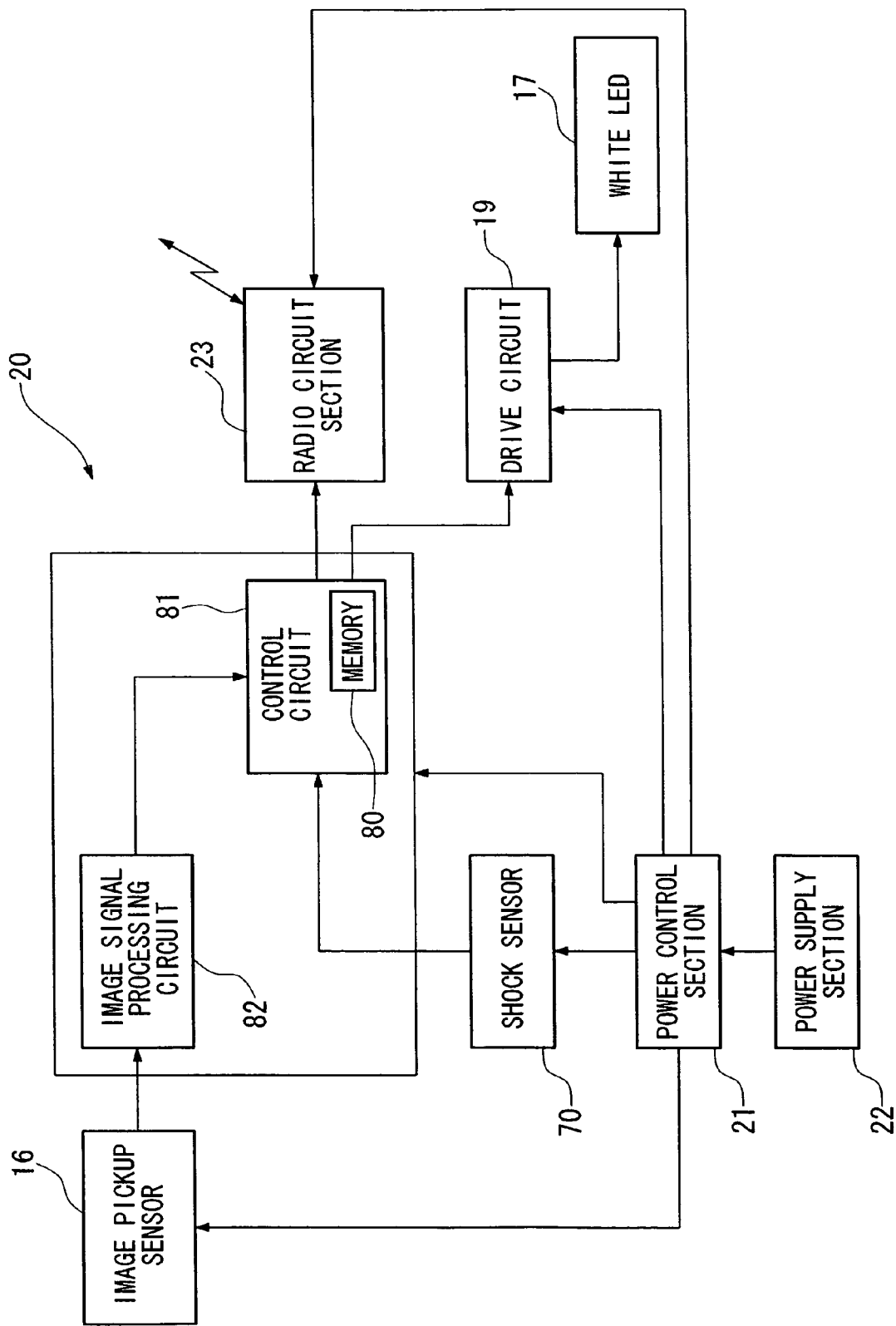
FIG. 6 is a block diagram showing an internal structure of the capsule endoscope according to a first embodiment of the present invention.
Figure 7:
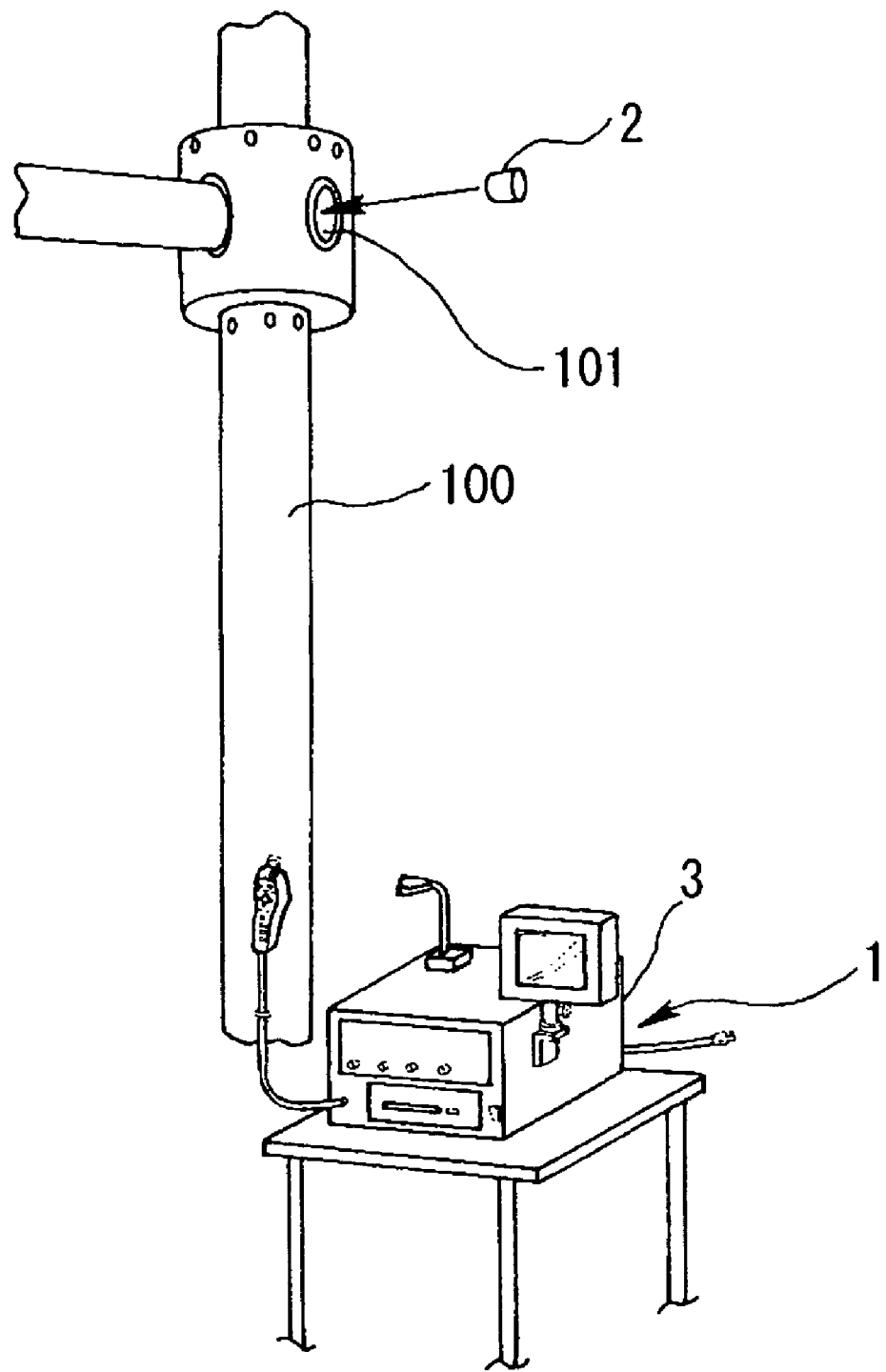
FIG. 7 is an explanatory view showing an example of the set up of the capsule endoscope according to a first embodiment of the present invention.
Figure 8:
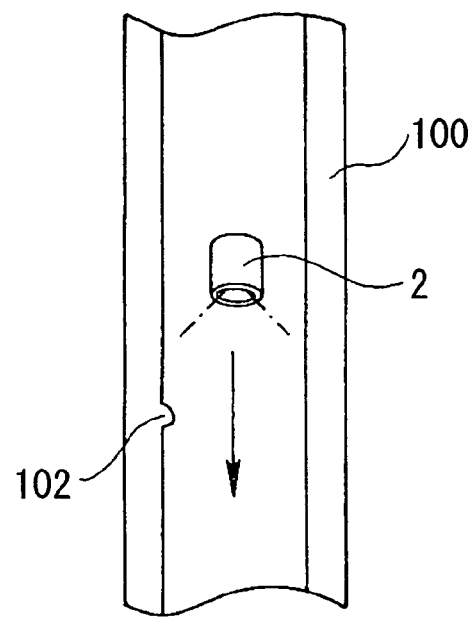
FIG. 8 is an explanatory view showing a capsule endoscope falling while observing an object being examined according to a first embodiment of the present invention.
Figure 9:
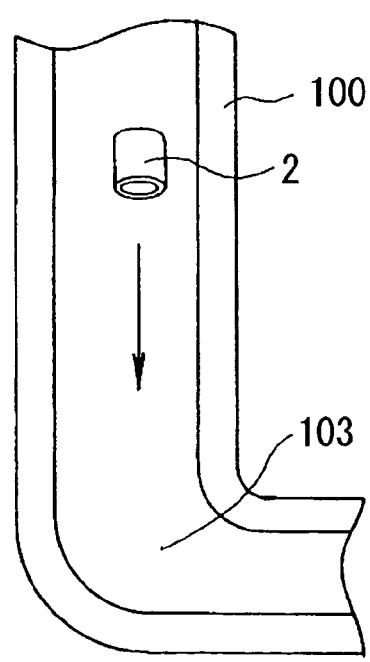
FIG. 9 is an explanatory view showing a capsule endoscope arriving in a vicinity of a deepest portion of an object being examined according to the first embodiment of the present invention.
Figure 10:
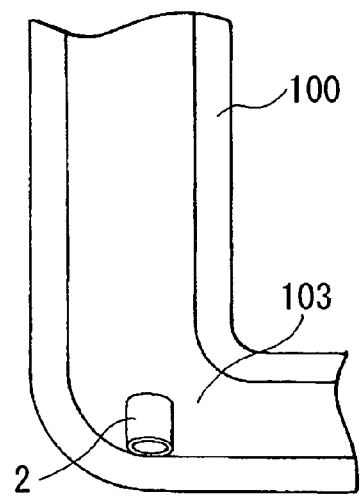
FIG. 10 is an explanatory view showing a capsule endoscope colliding against a deepest portion of an object being examined according to the first embodiment of the present invention.
Figure 11:
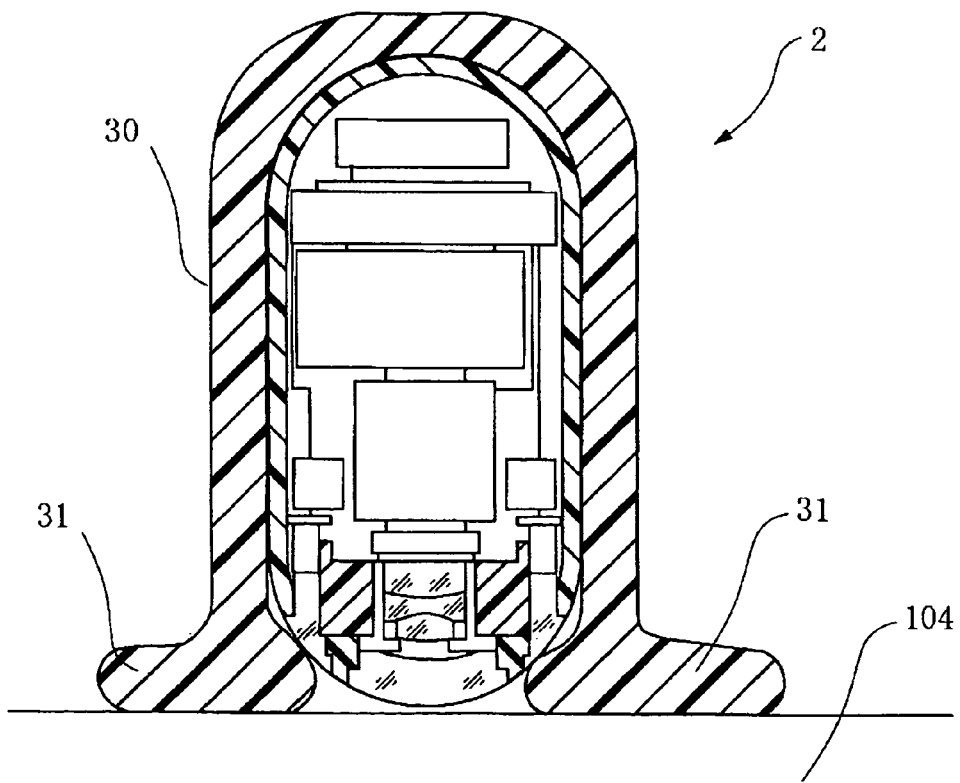
FIG. 11 is an explanatory view showing details of a moment of impact of a capsule endoscope according to the first embodiment of the present invention.
Figure 12:
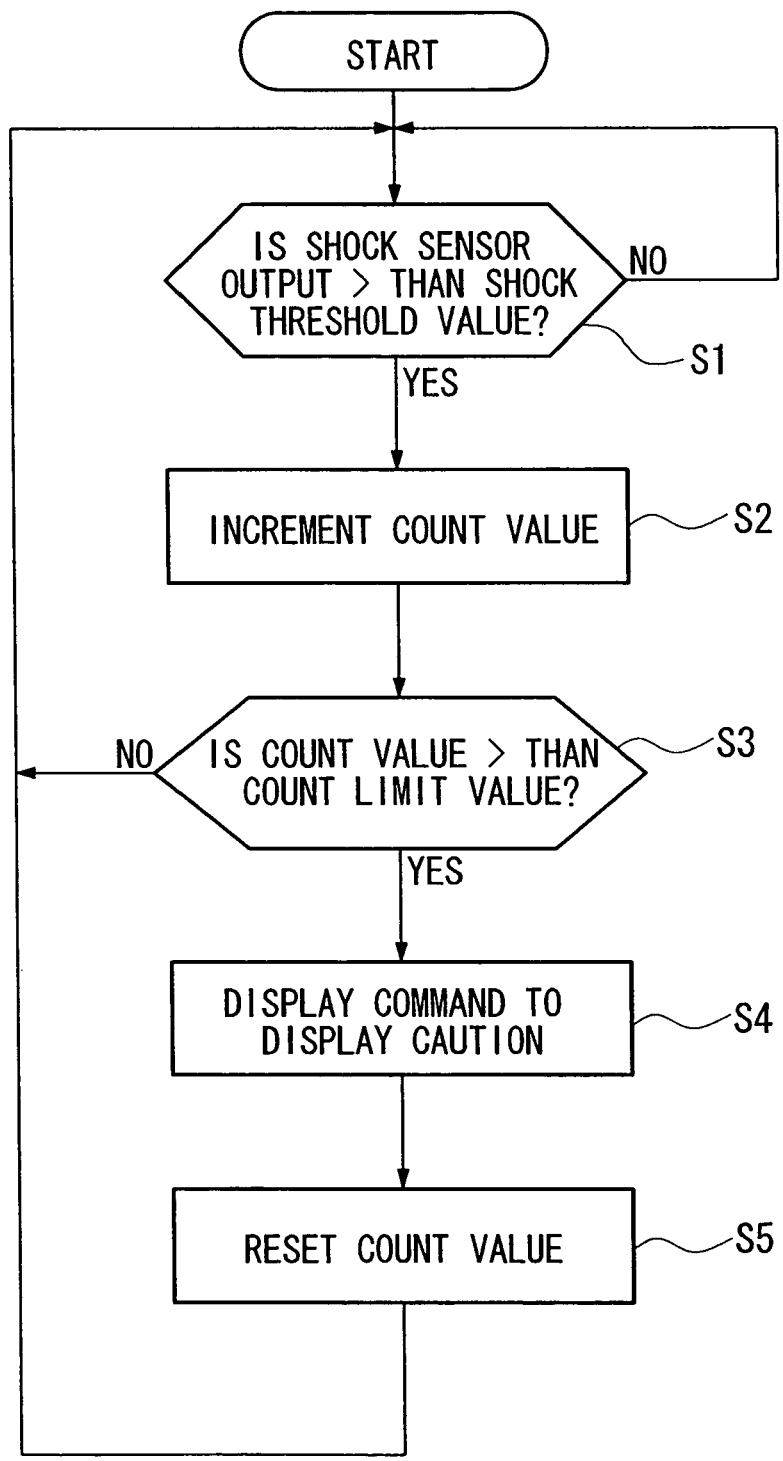
FIG. 12 is a flow chart showing processing on a shock sensor output according to the first embodiment of the present invention.
Figure 13:
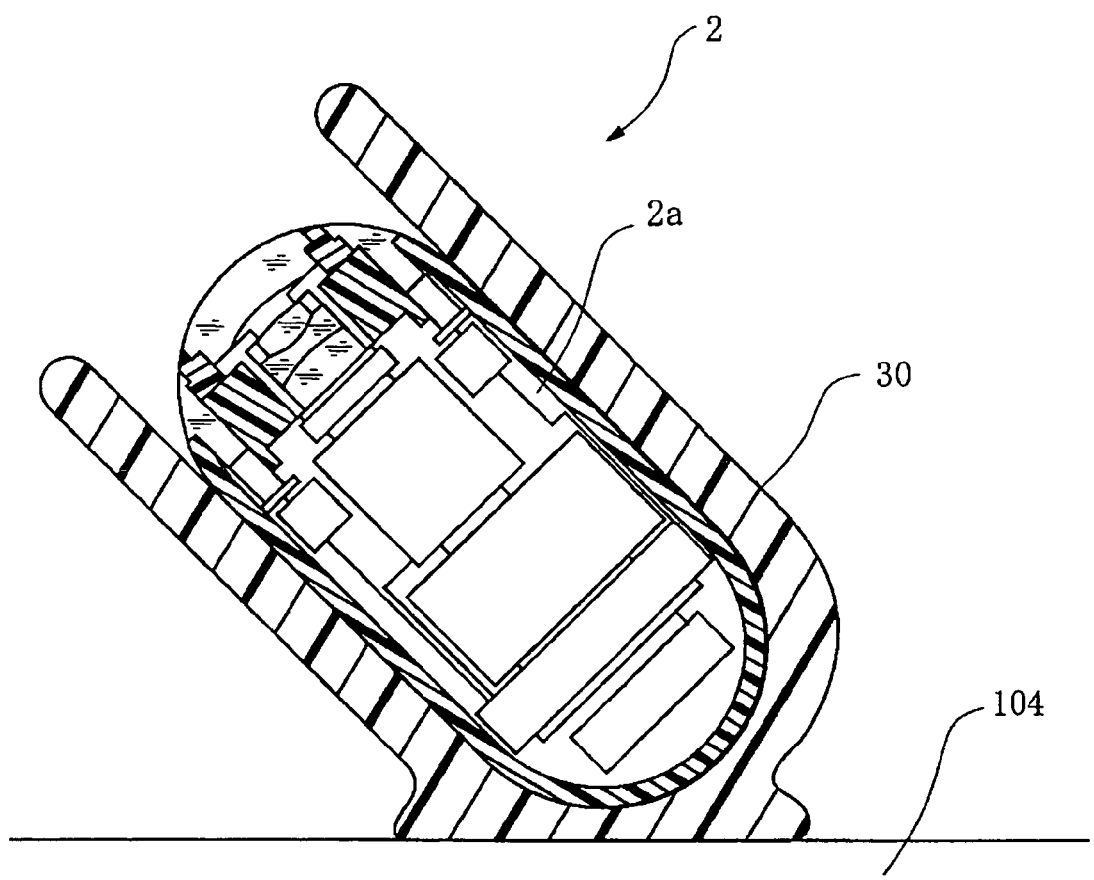
FIG. 13 is an explanatory view showing details of a moment of impact from another direction of the capsule endoscope according to the first embodiment of the present invention.
Figure 14:
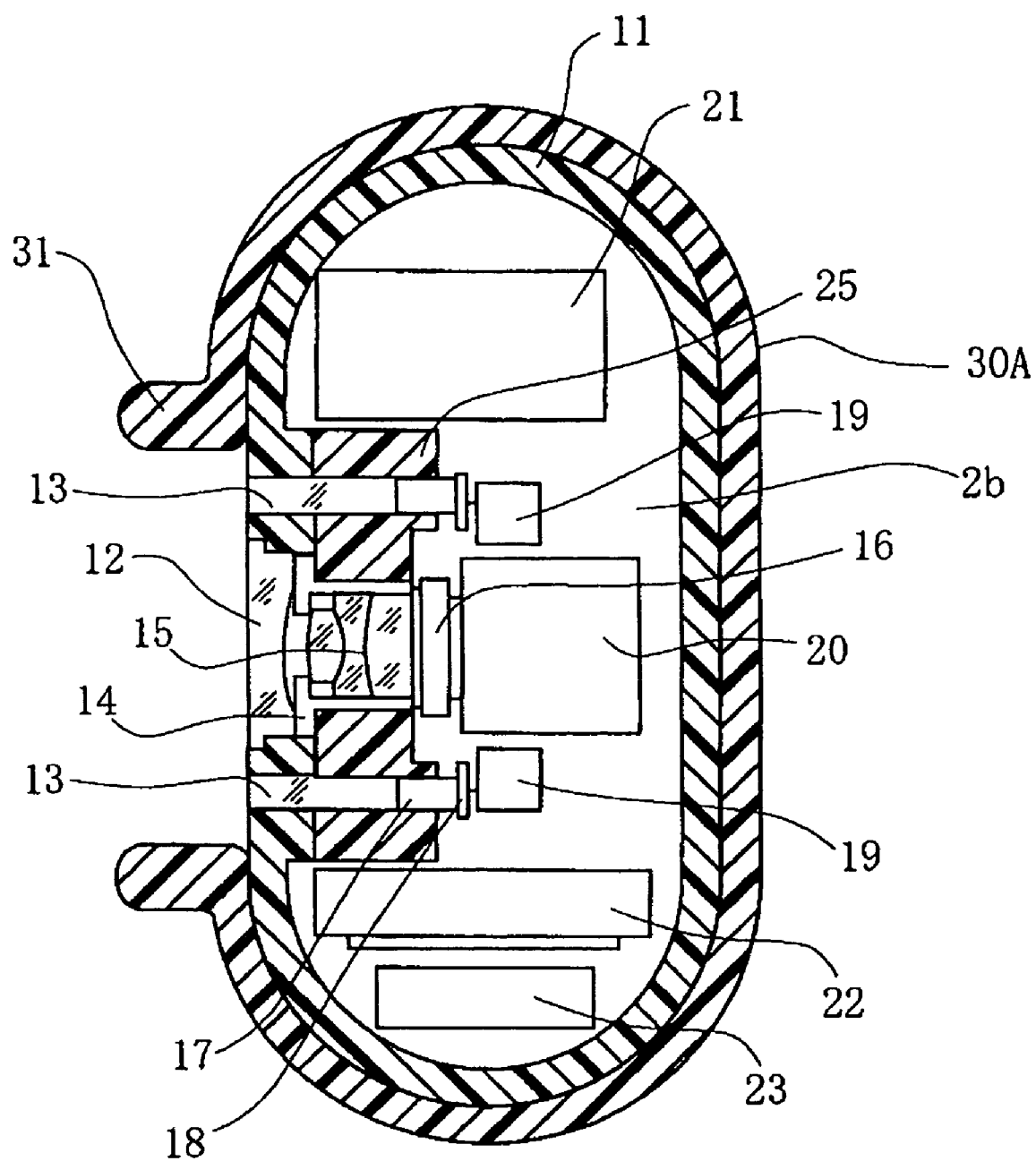
FIG. 14 is an explanatory view showing a side looking type of capsule endoscope according to the first embodiment of the present invention.
Figure 15:
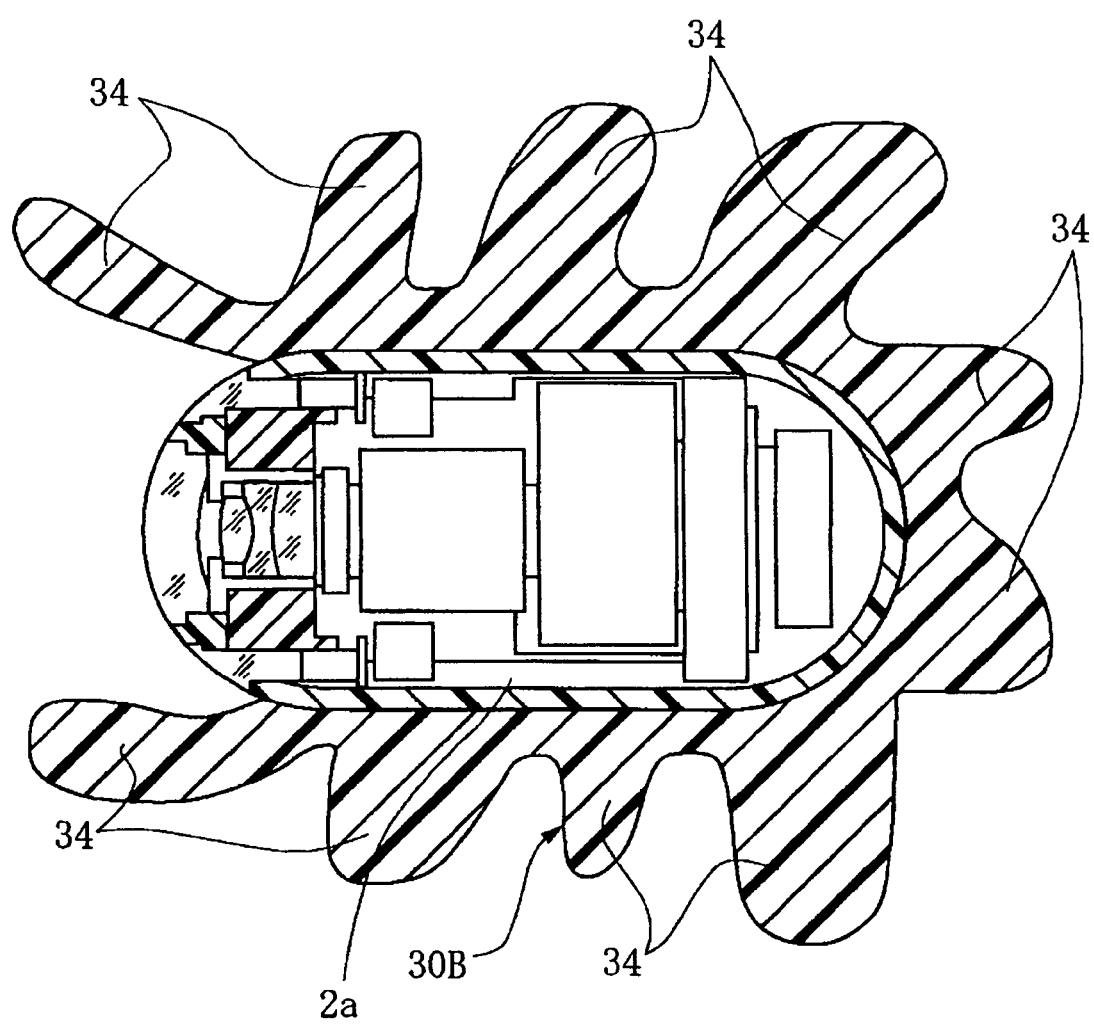
FIG. 15 is an explanatory view showing a variant example of a protective body according to the first embodiment of the present invention.

Embodiments of the present invention will now be described with reference made to the drawings. FIGS. 1 to 15 relate to the first embodiment of the present invention. FIG. 1 is a structural view of a capsule endoscope apparatus. FIG. 2 is a structural view of the capsule endoscope. FIG. 3 is an explanatory view showing an outer diameter of the capsule endoscope. FIG. 4 is an explanatory view showing an inner diameter of a protective body. FIG. 5 is an explanatory view showing another example of a mounting of the protective body. FIG. 6 is a block diagram showing an internal structure of the capsule endoscope. FIG. 7 is an explanatory view showing an example of the set up of the capsule endoscope. FIG. 8 is an explanatory view showing a capsule endoscope falling while observing an object being examined. FIG. 9 is an explanatory view showing a capsule endoscope arriving in a vicinity of a deepest portion of an object being examined. FIG. 10 is an explanatory view showing a capsule endoscope colliding against a deepest portion of an object being examined. FIG. 11 is an explanatory view showing details of a moment of impact of a capsule endoscope. FIG. 12 is a flow chart showing processing on a shock sensor output. FIG. 13 is an explanatory view showing details of a moment of impact from another direction of the capsule endoscope. FIG. 14 is an explanatory view showing a side looking type of capsule endoscope. FIG. 15 is an explanatory view showing a variant example of a protective body according to the first embodiment of the present invention.

The capsule endoscope apparatus 1 shown in FIG. 1 is provided with a capsule endoscope 2 that is inserted inside a pipe in a plant or inside a gas turbine or the like and transmits image signals taken of the interior thereof by radio, and an apparatus body 3 receives and processes image signals that are radio transmitted from the capsule endoscope 2.

The apparatus body 3 is provided with an antenna section 4 for transmitting and receiving radio signals with the capsule endoscope 2, a processing section 5 that processes images received by the antenna section 4 such that they can be displayed on a monitor 6, a recording section 7 that records images on media such as a magneto-optic disk, and a controller 8 in the form of an operating section that issues commands relating, for example, to the display brightness on the monitor 6, magnification and reduction, movement of the display area, freezing, recording and the like. In addition, the apparatus body 3 is provided with a power cable 9 and an on switch 10 for turning on the apparatus body 3.

Next, a description will be given of the capsule endoscope 2. As is shown in FIG. 2, the capsule endoscope 2 is formed by packaging a protective body 30 (described below) that protects the capsule endoscope body 2a from shocks caused by collisions with surrounding objects around the exterior of the capsule endoscope body 2a. The capsule endoscope body 2a is provided with a case 11, which is shaped substantially as a circular cylinder whose rear end side has been rounded into a spherical shape, that serves as an exterior packaging body for the capsule endoscope body 2a itself, and a lens cover 12 and light emitting diode (LED) covers 13 that are provided continuously with the case 11 at the distal end side of the case 11.

An objective optical system 15 that is held in a lens frame 14 is placed at a position facing the lens cover 12 inside the case 11. An image pickup sensor 16 formed by a CCD or CMOS or the like is placed at the focusing position of this objective optical system 15. A white LED 17 that serves as a light source for illuminating the distal end side of the capsule endoscope 2 as well as a substrate 18 that is provided at an end portion of the white LED 17 are provided at a position facing the LED covers 13. A drive circuit 19 that causes the white LED 17 to emit light is connected to the substrate 18. A plurality of white LED 17, substrates 18, and drive circuits 19, are provided around the objective optical system 15.

At a rear end side of the image pickup sensor 16 are mounted a control section 20 that primarily performs the driving of the image pickup sensor 16 and the processing of image signals from the image pickup sensor 16, a power control section 21 that controls power from a power supply section 22 and feeds power to the control section 20 and the drive circuit 19, the power supply section 22 that is formed by a button cell or the like, and a radio circuit section 23 that transmits by radio signals processed by the control section 20 to the antenna section 4 of the apparatus body 3.

Moreover, in the capsule endoscope 2 shown in FIG. 2, weighted portions 24 are placed in a plurality of locations towards the distal end side in the interior of the capsule endoscope body 2a so that the center of gravity of the capsule endoscope 2 is towards the distal end thereof. A shock sensor 70 that detects the shock when the capsule endoscope 2 collides against a wall surface or the like inside an object being examined into which it has been inserted and notifies the control section 20 about this shock is provided at a rear end side of the image pickup sensor 16.

Note that the weighted portions 24 and the shock sensor 70 are not an indispensable part of the structure of the capsule endoscope body 2a, and hereinafter are omitted from the drawings of the interior of the capsule endoscope body 2a when this is appropriate. Note also that the lens frame 14, the objective optical system 15, the image pickup sensor 16, the white LED 17, the substrate 18, the drive circuit 19, the control section 20, the power control section 21, the power supply section 22, and the radio circuit section 23 are bonded or anchored to a main body trunk portion 25 provided inside the case 11.

A protective body 30 is provided so as to enclose the case 11 apart from the lens cover 12 and the LED covers 13. The protective body 30 has an open circular cylinder portion 31 that protrudes as a circular cylinder on the lens cover 12 and LED cover 13 side, and a trunk portion 32 that covers the case 11. The protective body 30 is formed by a material having elasticity that is formed from a soft resin such as urethane, polyethylene, or vinyl chloride.

The protective body 30 is attached to the capsule endoscope body 2a and is fixed in place by pressure insertion, an engaging portion, an adhesive or the like such that an amount of protrusion L of the circular cylinder portion 31 does not obstruct a range of vision W of the objective optical system 15. For example, if the protective body 30 is fixed by pressure insertion to the capsule endoscope body 2a, as is shown in FIG. 3 and FIG. 4, the interior diameter $\phi b$ of the protective body 30 is smaller than the exterior diameter $\phi a$ of the case 11 and is a size that enables the case 11 to be pressure inserted into the protective body 30. Note that the thickness of the protective body 30 is set to a thickness that does not obstruct radio signals from the radio circuit section 23.

When the protective body 30 is attached to the capsule endoscope body 2a without using pressure insertion, for example, as is shown in FIG. 5, it is also possible to provide a concave portion 33A on an outer circumferential side of the case 11 of the capsule endoscope body 2a and a convex portion 33B on an inner surface side of the protective body 30, and to fix the protective body 30 in place by engaging the concave portion 33A with the convex portion 33B. In this case, the concave portion 33A and the convex portion 33B are each placed around the entire circumference in the circumferential direction or in a portion thereof. If they are placed in a portion thereof, there is no problem in providing a plurality of concave portions 33A and convex portions 33B. Attaching the protective body by engaging the concave portion 33A with the convex portion 33B can be employed instead of using pressure insertion in each of the embodiments described below.

Here, a description will be given of the internal control system of the capsule endoscope 2, in particular, of the internal structure of the control section 20. As is shown in FIG. 6, power from the power supply section 22 is controlled by the power control section 21 and is supplied to the image pickup sensor 16, the drive circuit 19 that drives the white LED 17, the control section 20, the radio circuit section 23, and the shock sensor 70. The control section 20 is a function section that processes signals from the image pickup sensor 16 and the shock sensor 70, and outputs control commands to the drive circuit 19 and the radio circuit section 23. The control section 20 has a memory 80 that holds a shock threshold value for the shock sensor 70, a count value (i.e., number of usages) of the shock sensor 70, and a count limit value, and is provided with a control circuit 81 that governs the overall control of the capsule endoscope 2, and an image signal processing circuit 82 that performs image processing on signals output from the image pickup sensor 16 and sends them to the control circuit 81.

As is described below, a capsule endoscope 2 having the above described structure is inserted inside an examined object and is dropped so as to collide against a wall surface of a curved portion, for example, an elbow wall surface or the like inside the examined object. In order to repeat this type of collision operation, it is desirable that the protective body 30 be replaced after it has performed a fixed number of operations.

Therefore, firstly, the power supply cable 9 is connected and the on switch 10 is placed in an ON state. The number of usages (i.e., the count value) recorded in the memory 80 inside the control circuit 81 of the capsule endoscope 2 is read by radio communication by the apparatus body 3 of the capsule endoscope apparatus 1. Consequently, it is confirmed whether or not it is necessary to replace the protective body 30. As a result of this, if it is not necessary to replace the protective body 30, as is shown in FIG. 7, when the capsule endoscope apparatus 1 is used, the apparatus body 3 is placed as close as possible to the instrument being examined (i.e., to the examined object) so that there is no obstruction to radio communication from the capsule endoscope 2.

It is then confirmed whether or not there are any problems regarding the condition of radio communication between the capsule endoscope 2 and the apparatus body 3. At this time, if the images contain a lot of noise, the apparatus body 3 is moved in order to avoid radio wave interference and once a position where the image condition poses no problem to examination is achieved, examination preparations are made. If the image on the monitor 6 needs to be adjusted due to the brightness of the area being examined or to the examination range or the like, this adjustment is made using the controller 8.

Next, if the instrument that is being examined is, for example, a pipe of a plant facility or the like, the lid of a valve provided partway along the pipe 100 is opened and the capsule endoscope 2 is inserted into the pipe 100 from an aperture portion 101 thereof. Consequently, as is shown in FIGS. 8 and 9, the capsule endoscope 2 falls through the interior of the pipe 100 due to gravity while observing locations where damage has been caused by foreign matter or the like.

As the capsule endoscope 2 falls it approaches the deepest portion (here, this is an elbow 103) until, finally, as is shown in FIG. 10, it collides against the wall surface of the elbow 3. At the moment of this collision, if the weighted portions 24 are provided inside the capsule endoscope body 2a, because the center of gravity is placed towards the distal end due to the weighted portions 24, as is shown in FIG. 11, the circular cylinder portion 31 of the protective body 30 collides against a wall surface 104 and is elastically deformed so as to become a shock absorbing portion and protect each portion inside the case 11 as well as the LED cover 13 and the lens covers 12.

Once the examination is completed, a valve located in a downstream area from the aforementioned valve is opened and, by supplying a fluid body such as water from an upstream location, the capsule endoscope 2, which has ended its examination, is recovered from the downstream valve. For this recovery, a normally known endoscope that has a narrow, elongated insertion portion may be used. In this case, the capsule endoscope can also be recovered using a channel or the like that opens at the distal end of the insertion portion of the normal endoscope.

In this examination, if the protective body 30 of the capsule endoscope 2 is restored elastically and returns to its original shape, it can be used in that state. Moreover, although there are cases in which cuts or cracks may be generated in the protective body 30 by the shock, because the protective body 30 is soft and is formed from an elastic material, in such cases, it is possible to remove the protective body 30 from the capsule endoscope body 2a and place a new protective body 30 around the case 11.

The need for replacing the protective body 30 may be determined based on an output value from the shock sensor 70 with the need for replacement then bought to the user's attention. Next, a description will be given of the processing on an output from the shock sensor 70 using the flow chart shown in FIG. 12.

The processing shown in FIG. 12 is processing to urge the user to replace the protective body 30 using the number of times (i.e., the count value) that an output from the shock sensor 70 when the capsule endoscope 2 collides against a wall surface or the like has exceeded a shock threshold value that is set in advance. Here, the shock threshold value of the shock sensor 70 and the count limit value are transmitted in advance by radio communication to the capsule endoscope 2 and are recorded in the internal memory 80 of the control circuit 81.

Specifically, firstly, in step S1, an output from the shock sensor 70 when the capsule endoscope 2 collides against a wall surface or the like of an examined object is read and whether or not this output value exceeds a shock threshold value is checked. If the output from the shock sensor 70 exceeds the shock threshold value the routine moves to step S2 and the count value stored in the memory 80 is incremented.

Next, the routine moves to step S3 and whether or not the count value exceeds the count limit value is checked. If the result of this is that the count value is equal to or less than the count limit value, the routine returns to step S1 and the output from the shock sensor 70 is monitored. If the count value exceeds the count limit value, the routine moves to step S4 and a command to display a caution display is notified by radio to the apparatus body 3. In the apparatus body 3, this command is received and a caution display urging the user to replace the protective body 30 is displayed on the monitor 6. The routine then moves from step S4 to step S5, the count value in the memory 80 is reset and the routine returns to step S1.

Note that a description is given of when the count limit value is held in the memory 80 in the control circuit 81 of the capsule endoscope 2 and the above processing is executed on the capsule endoscope 2 side. However, it is also possible for the count limit value to be held in the apparatus body 3 and, each time the output from the shock sensor 70 exceeds the shock threshold value, for the count value to be sent to the apparatus body 3 by radio communication from the capsule endoscope 2 so that the processing shown in FIG. 12 (i.e., the processing of step S2 and beyond) is executed on the apparatus body 3 side.

In this way, by providing the protective body 30 on the capsule endoscope 2, and by the protective body 30 further becoming a shock absorbing body, the instruments inside the capsule endoscope body 2a as well as the case 11, the lens cover 12 and the LED covers 13 can be protected. In particular, in an examination in which the examined object is a hard material such as is seen when the capsule endoscope is used in industrial applications, by providing the protective body 30 in the form of a shock absorbing body as a precaution against the capsule endoscope 2 colliding against the examined object due to gravity or the like, it is possible to recover the capsule endoscope body 2a in an undamaged state, and use it for the next examination. In other words, the effect is achieved that it is possible to reduce unnecessary costs by reusing the capsule endoscope body 2a.

Furthermore, because the protective body 30 is used, not only is the effect obtained that the wall surface of the examined object (for example, the inside wall of a pipe) is not damaged, but it is possible to protect the capsule endoscope body 2a against shocks that occur if it is dropped on the floor through careless handling before or after use, or if it is knocked against machinery or equipment or the like in the vicinity, and to thereby avoid the generation of malfunctions.

Note that because the protective body 30 also protects portions other than the portions protected by the circular cylinder portion 31, it is effective even when the weighted portions 24 are not specially provided in the capsule endoscope body 2a. Regardless of the position of the center of gravity, as is shown in FIG. 13, the protective body 30 protects the capsule endoscope body 2a when it collides against the wall surface 104 of the examined body, and prevents any problem occurring in the internal instruments inside the capsule endoscope 2.

The optical system mounted in the capsule endoscope body 2a is not limited to a direct view type that observes only the longitudinal axial direction of the capsule endoscope 2, such as that shown in FIG. 2, and may be an oblique view type that observes in an oblique direction, a side view type that observes in a side surface direction, or may be both types. FIG. 14 is a view showing a side view type. In FIG. 14, a protective body 30A, in which a circular cylinder portion 31 is provided in a side surface direction to correspond to a capsule endoscope body 2b, is packaged around the capsule endoscope body 2b in which an optical system, an image pickup system, and an illumination system are arranged in the side surface direction. The orientations of the optical system, the image pickup system, and the illumination system of the side view type of capsule endoscope body 2b differ from those of the direct view type of capsule endoscope body 2a. In accordance with this, the placement of the drive circuit 19, the control section 20, the power control section 21, the power supply section 22, and the radio circuit section 23 are slightly different, however, the fundamental structure is the same.

Furthermore, in the circular cylinder portion 31 of the protective body 30, protrusions 34 that correspond to the circular cylinder portion 31 may be provided not only around the lens cover 12 and the LED covers 13, but, as is shown in FIG. 15, may be provided as a protective body 30B that naturally protrudes around the lens cover 12 and the LED covers 13 but also covers the entire capsule endoscope body 2a.

Figure 16:
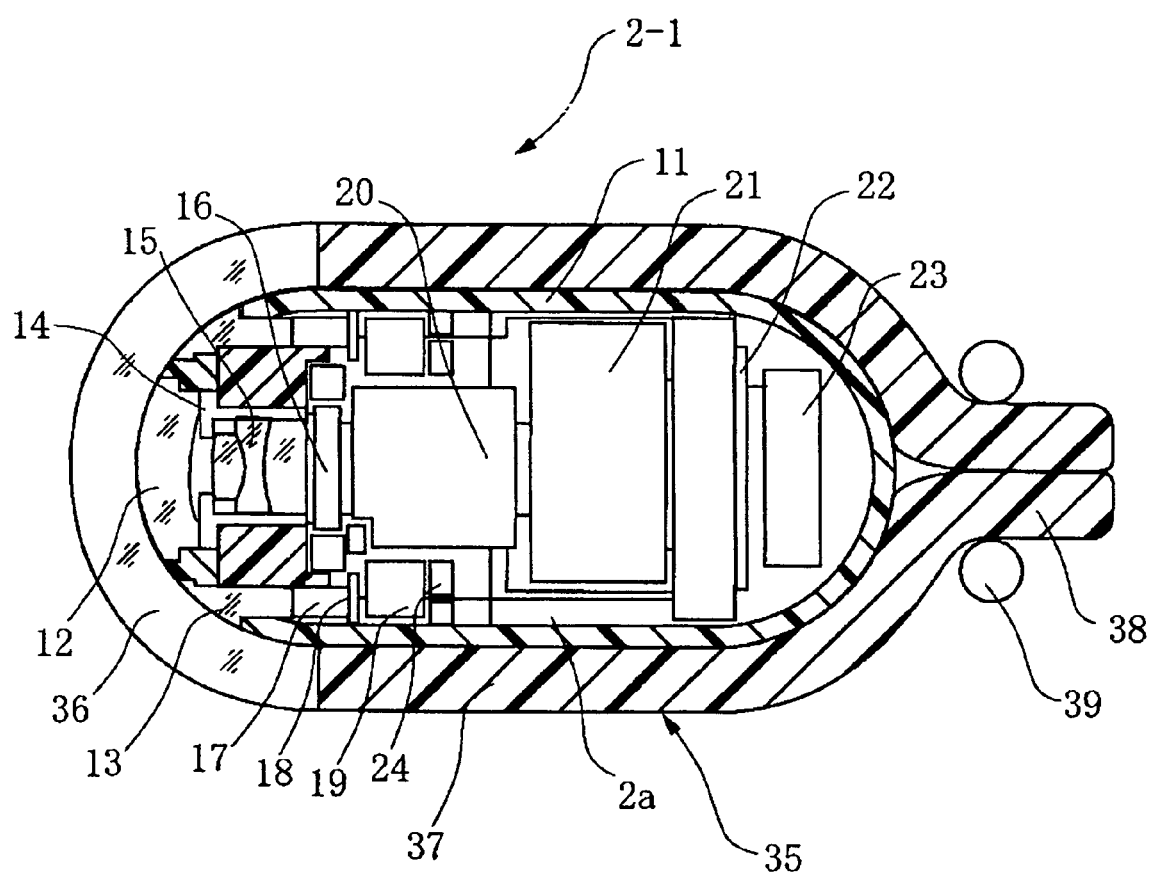
FIG. 16 is a structural view of a capsule endoscope according to a second embodiment of the present invention.
Figure 17:
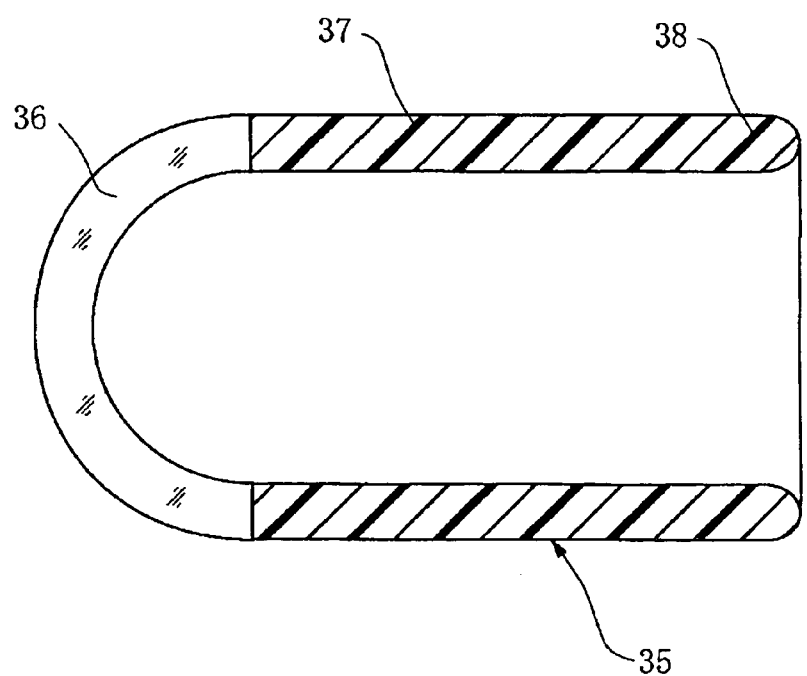
FIG. 17 is an explanatory view of a protective body unit according to a second embodiment of the present invention.
Figure 18:
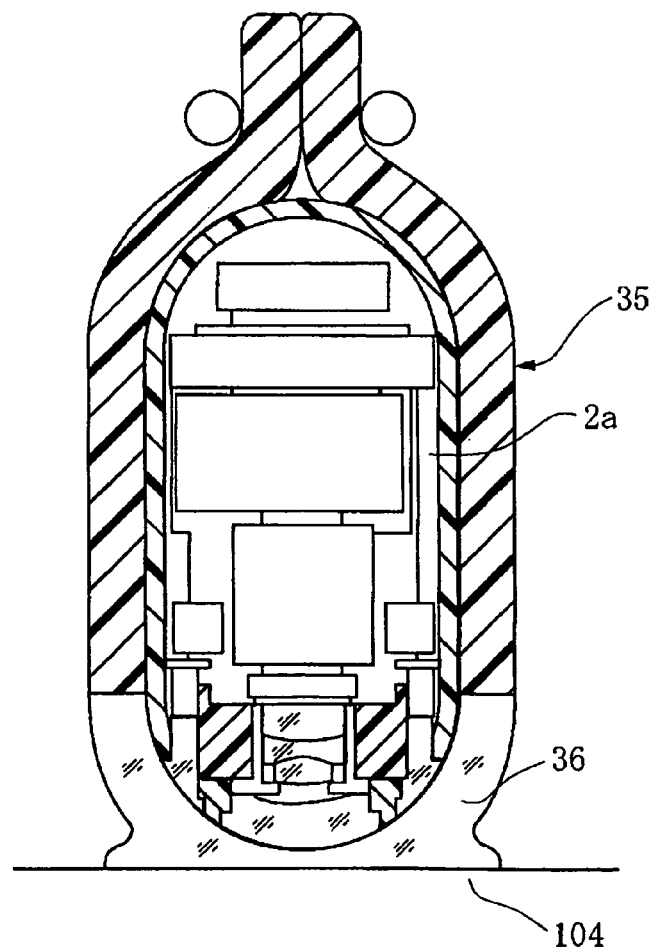
FIG. 18 is an explanatory view showing details of a moment of impact of a capsule endoscope according to a second embodiment of the present invention.
Figure 19:
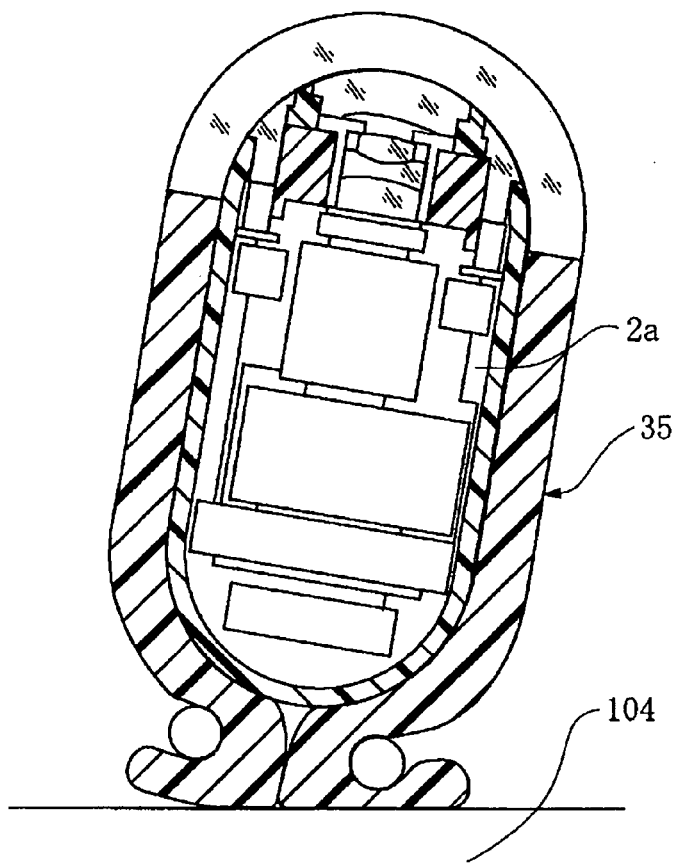
FIG. 19 is an explanatory view showing details of a moment of impact from another direction of the capsule endoscope according to a second embodiment of the present invention.
Figure 20:
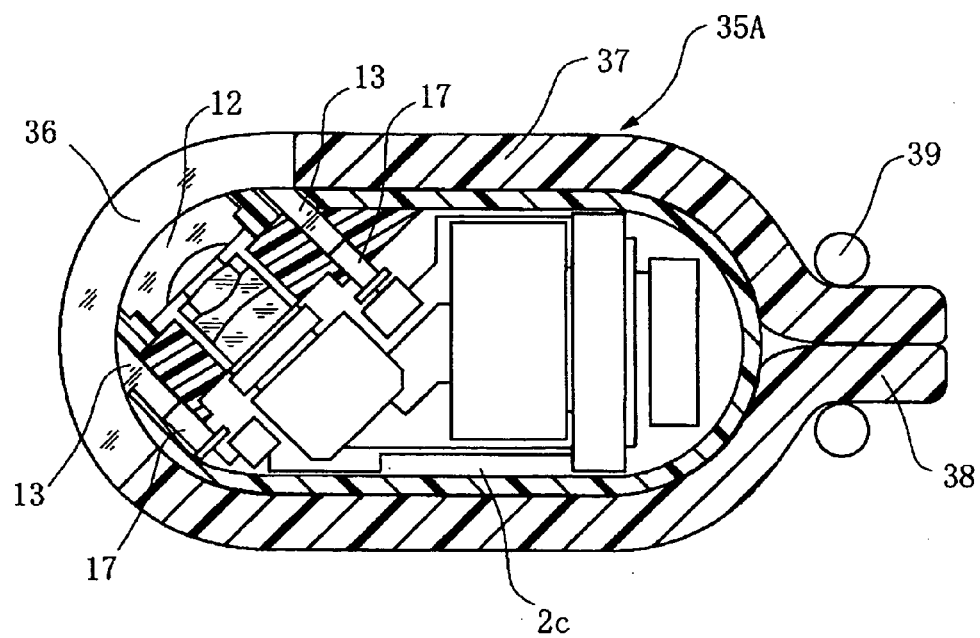
FIG. 20 is an explanatory view showing an oblique view type of capsule endoscope according to a second embodiment of the present invention.

Next, the second embodiment of the present invention will be described. FIGS. 16 to 20 relate to the second embodiment of the present invention. FIG. 16 is a structural view of a capsule endoscope. FIG. 17 is an explanatory view of a protective body unit. FIG. 18 is an explanatory view showing details of a moment of impact of a capsule endoscope. FIG. 19 is an explanatory view showing details of a moment of impact from another direction of the capsule endoscope. FIG. 20 is an explanatory view showing an oblique view type of capsule endoscope. Note that members that have the same operation and effect as those in the above described first embodiment are given the same symbols and a description thereof is omitted.

As is shown in FIG. 16, the capsule endoscope 2-1 of the second embodiment is provided with a bag shaped protective body 35 that covers the case 11, the lens cover 12, and the LED covers 13 of the capsule endoscope body 2a. The protective body 35 has a transparent portion 36 that faces the lens cover 12 and the LED covers 13 and does not obstruct the field of vision or the illumination thereof, a bag body 37 that is integrally bonded with the transparent portion 36, and a binding band 39 that binds the bag end portion 38 of the rear end of the bag body 37.

Namely, the protective body 35 taken by itself is configured such that a bag end portion 38 at the rear end of the bag body 37 is open, as is shown in FIG. 17, and the transparent portion 36 and the bag body 37 are integrated by adhesive, fusion, integral molding or the like. The capsule endoscope body 2a is inserted from the open portion of the bag end portion 38 and the bag end portion 38 is then bound by the binding band 39.

Note that the inner diameter of the protective body 35 may be smaller than (in the case of pressure insertion) or larger than the outer diameter of the capsule endoscope body 2a, and the protective body 35 is packaged tightly around the capsule endoscope body 2a using the binding band 39. The transparent portion 36 and the bag body 37 may be formed from the same material or from different materials, however, it is preferable that both are formed from a material having the same elasticity as the pliable resin of the protective body 30 of the first embodiment.

In the second embodiment, firstly, the capsule endoscope body 2a is covered by the protective body 35. It is then confirmed that the transparent cover 36 is not obstructing the lens cover 12 and the LED covers 13. The bag end portion 38 is then bound by the binding band 39 and is fastened. As was described for the first embodiment, the apparatus body 3 is then positioned close to the instrument being examined (i.e., the examined object) so that there is no obstruction to radio communication, and an examination of the interior of a pipe or the like of a plant facility is performed.

In this examination, in the same way as is shown in FIG. 10, when the capsule endoscope 2-1 collides against a wall surface of the examined instrument, as is shown in FIG. 18, the transparent portion of the capsule endoscope 2-1 elastically deforms when it collides against the wall surface 104 so that the capsule endoscope 2-1 itself deforms in the manner of a shock absorbing body. Accordingly, the shock from the impact is absorbed by the protective body 35 and there is no effect on the capsule endoscope body 2a itself.

In the above described protective body 30 of the first embodiment, if the wall surface is not flat but rises up in a conical configuration, the possibility exists that the lens cover 12 will contact the wall surface before the circular cylinder portion 31 of the protective body 30. To counter this, in the protective body 35 of the present embodiment, because the transparent portion 36 covers the entire front surface, the effect is achieved that it is possible to protect the lens cover 12 and the LED covers 13 more reliably.

Moreover, even if the weighted portions 24 have not been specially provided inside the capsule endoscope body 2a so that the center of gravity is in no particular position, because the protective body 35 covers the entire capsule endoscope 2-1, as is shown in FIG. 19, regardless of the manner in which it strikes the wall surface 104, because the protective body 35 protects the capsule endoscope body 2a there is no problem with the instruments inside the capsule endoscope body 2a.

The optical system mounted in the capsule endoscope body 2a is not limited to a direct view type that observes only the longitudinal axial direction of the capsule endoscope 2, and may be an oblique view type that observes in an oblique direction, a side view type that observes in a side surface direction, or may be both types. In this case, the transparent portion 36 may be provided facing the lens cover 12 and LED covers 13 of the optical system at a position where it does not obstruct the field of vision or illumination thereof.

FIG. 20 is a view showing an embodiment of an oblique view type. In FIG. 20, a protective body 35A, which is provided with a transparent portion 36 that faces the lens cover 12 and the LED covers 13, is packaged around a capsule endoscope body 2c in which the optical system and image pickup system are placed facing in an oblique direction. The oblique view type of capsule endoscope body 2c differs from the direct view type of capsule endoscope body 2a only in the orientation of the optical system, the image pickup system, and the illumination system, and the remainder of the main structure is the same.

Moreover, because the protective body 35 covers the entire capsule endoscope body, it is possible to do away with the case 11, the lens cover 12, and the LED covers 13 in the capsule endoscope main body and the protective body 35 may also perform these functions. In this case, the overall size of the capsule endoscope can be made smaller by the thickness of the case 11, the lens cover 12, and the LED covers 13.

Figure 21:
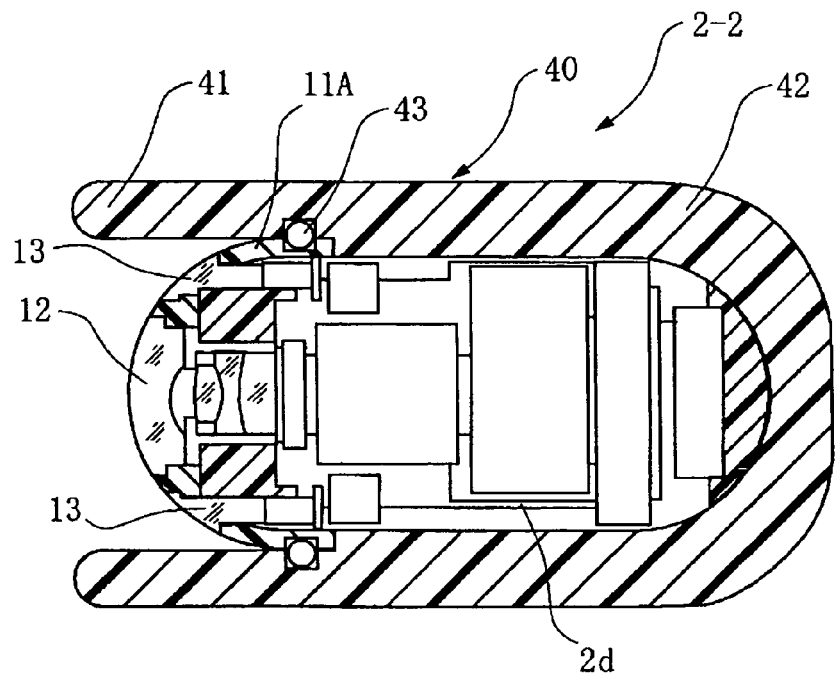
FIG. 21 is a structural view of a capsule endoscope according to a third embodiment of the present invention.

Next, the third embodiment of the present invention will be described. FIG. 21 relates to the third embodiment of the present invention and is a structural view of a capsule endoscope. Note that structure that has the same operation and effect as that in each of the above described embodiments is given the same symbol and a description thereof is omitted.

As is shown in FIG. 21, in the capsule endoscope 2-2 of the third embodiment, in a capsule endoscope body 2d having a case 11A whose rear end is open, there is provided a protective body 40 that replaces a portion of the case 11A and covers an opening portion of the case 11A. Other than the fact that the case 11A is different, the remainder of the structure of the capsule endoscope body 2d is fundamentally the same as that of the above described capsule endoscope body 2a.

The protective body 40 has a circular cylinder portion 41 that is open and protrudes in a circular cylinder shape on the lens cover 12 and LED covers 13 side, and a trunk portion 42 that covers an open portion of the rear end of the case 11A. As is described in the first embodiment, the protective body 40 is formed from a material having elasticity such as a soft resin. An O ring 43 is inserted between the rear end side of the case 11A of the capsule endoscope body 2d and the inner surface side of the protective body 40, and the interior is kept watertight by this O ring 43.

Note that, here, the O ring 43 also has the effect of locking the protective body 40 in place. It is also possible for the protective body 40 to be able to rotate freely around the case 11A on a portion of the O ring 43.

In the capsule endoscope 2-2 of the third embodiment, in the same way as in the above described first embodiment, the circular cylinder portion 41 absorbs the shock from a collision and is able to not only protect the capsule endoscope body 2d itself, but because a portion of the case 11A is made to double as the protective body 40, the capsule endoscope 2-2 has the advantage that the overall size thereof can be reduced. In the case of the present embodiment as well, if the circular cylinder portion 41 is damaged, it is sufficient if a new protective body 40 is attached.

Figure 22:
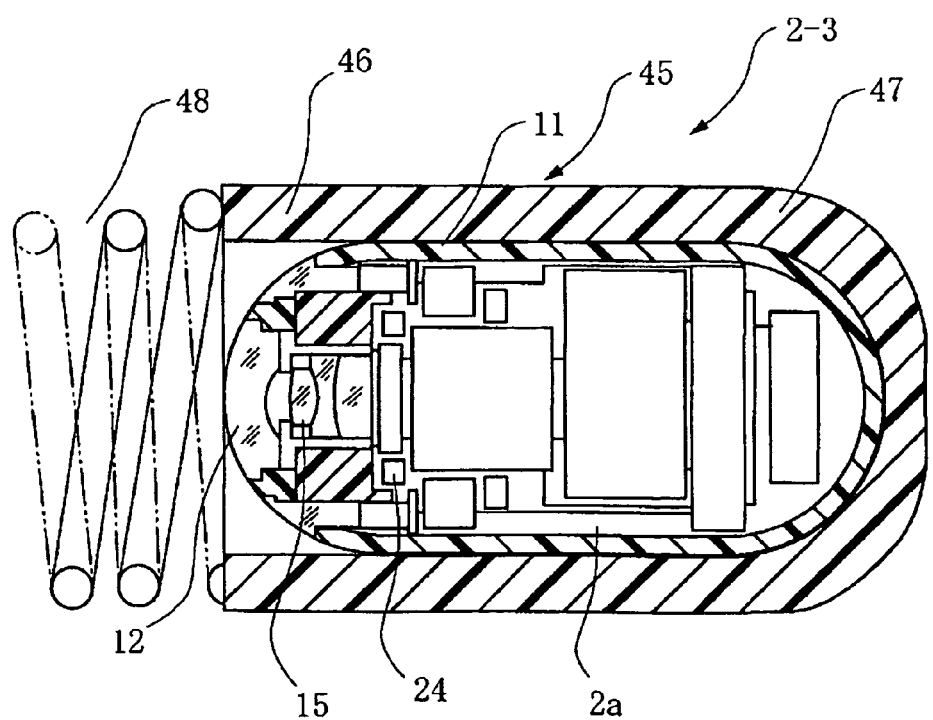
FIG. 22 is a structural view of a capsule endoscope according to a fourth embodiment of the present invention.
Figure 23:
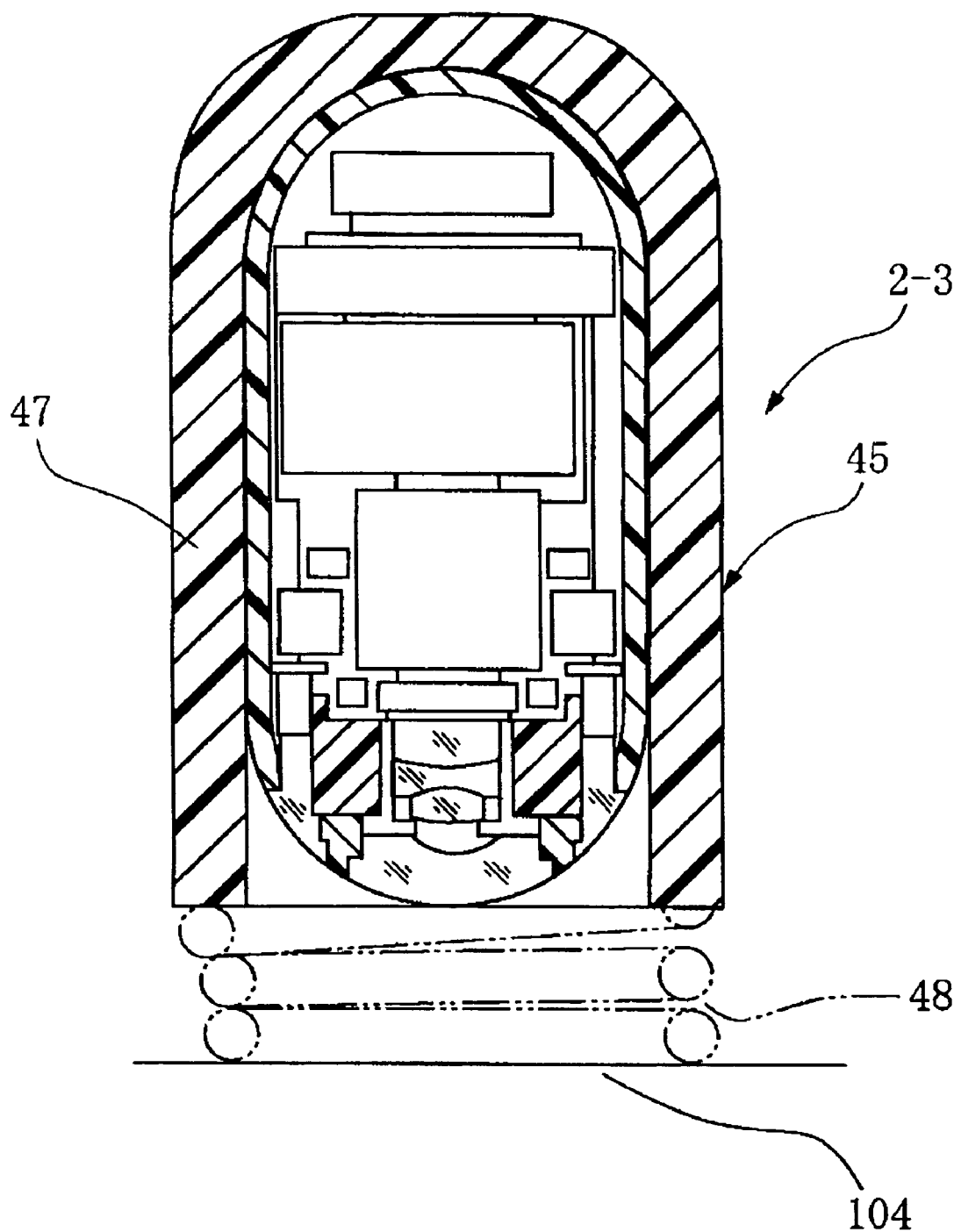
FIG. 23 is an explanatory view showing details of a moment of impact of a capsule endoscope according to a fourth embodiment of the present invention.

Next, the fourth embodiment of the present invention will be described. FIGS. 22 and 23 relate to the fourth embodiment of the present invention. FIG. 22 is a structural view of a capsule endoscope. FIG. 23 is an explanatory view showing details of a moment of impact of a capsule endoscope.

Because the protective body 30, the protective body 35 and the protective body 40 of each of the above described embodiments are formed from a soft material member, cases arise when they must be replaced during use due to cuts or cracks. The fourth embodiment does away with the need to replace the protective body by enabling the protective body to be used any number of times. Note that structure that has the same operation and effect as that in each of the above described embodiments is given the same symbol and a description thereof is omitted.

As is shown in FIG. 22, the capsule endoscope 2-3 of the fourth embodiment is provided with a spring portion 48 that protrudes outwards in front of a protective body 45 that covers the capsule endoscope body 2a. For the protective body 45, the protective body 30 of the first embodiment that has had the circular cylinder portion 31 thereof shortened, or the protective body 40 of the third embodiment that has had the circular cylinder portion 41 thereof shortened can be used. The protective body 45 shown in FIG. 22 has a circular cylinder portion 46 in which the circular cylinder portion 31 of the protective body 30 of the first embodiment has been shortened and that is open at substantially a distal end position of the lens cover 12, and a trunk portion 47 that covers the case 11. Note that the case 11 and the trunk portion 47 may be formed integrally, and the overall size of the capsule endoscope can be reduced.

A spring portion 48 is bonded to the circular cylinder portion 46 using a bonding device such as an adhesive or a coupling, and protrudes outwards so as not to obstruct the field of vision of the objective optical system 15. A weighted portion 24 is provided in the capsule endoscope body 2a so that the center of gravity is towards the distal end side thereof.

As is shown in FIG. 23, when the capsule endoscope 2-3 of the fourth embodiment drops inside an examined object during an examination and collides against the wall surface 104, because the distal end side is made to face downwards by the weighted portion 24, the spring portion 48 strikes against the wall surface 104. Accordingly, the shock from the impact is absorbed by a deformation of the spring portion 48, and there is no damage inflicted on the capsule endoscope body 2a itself.

The same effects are obtained in the fourth embodiment as those in each of the above described embodiments, however, if the spring portion 48 is created from metal wire, it is not easily damaged. Therefore, the effect is obtained that there is an increased probability that it will be able to be reused.

In this case, if the wire diameter of the wire used to form the spring portion 48 is made narrow so that the springback effect thereof is lowered, the shock imparted to the instrument being examined is reduced. Accordingly, at this time, the shock can be absorbed by increasing the number of coils so as to extend the length of the spring portion 48. Furthermore, although the durability thereof is deteriorated, the same effects are obtained if the material used to form the spring portion 48 is a resin material. If the spring portion 48 is damaged, it is sufficient if only the spring portion 48 is replaced.

Note that the protective body 30B shown in FIG. 15 that was described in the first embodiment is able to achieve the same effects if each of the protrusions 34 has an equivalent configuration to that of the spring portion 48.

Figure 24:
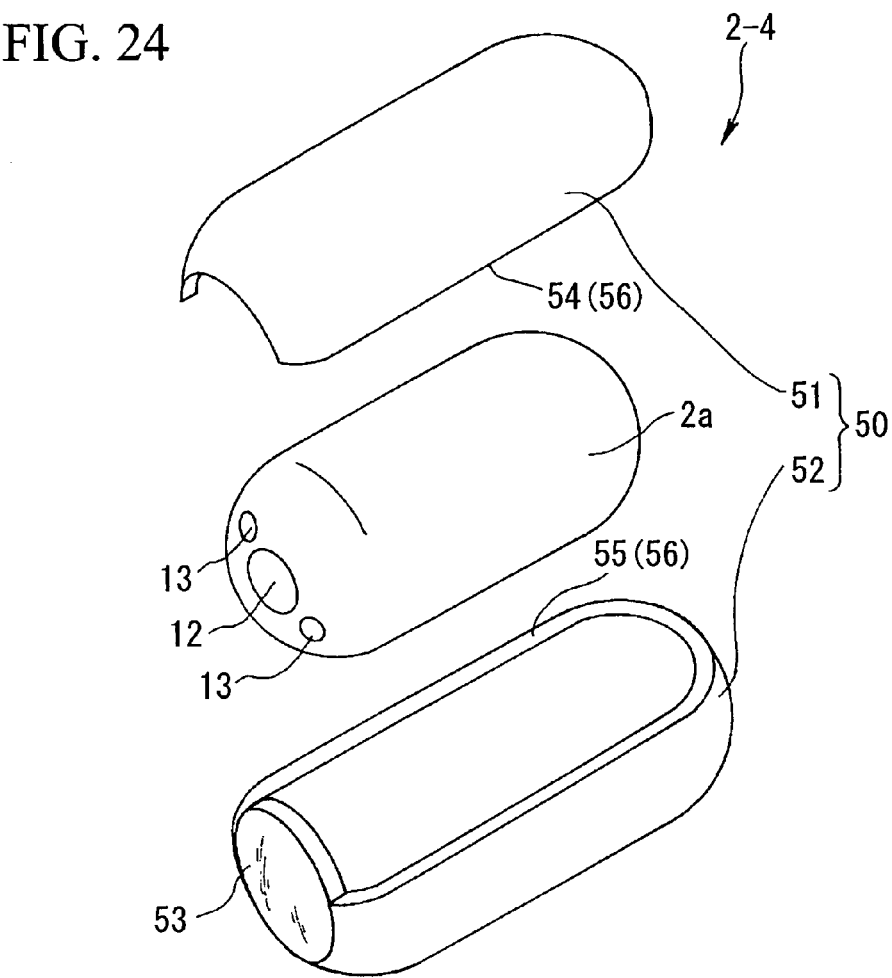
FIG. 24 is a perspective view showing a relationship between a protective body and a capsule endoscope body according to a fifth embodiment of the present invention.

Next, the fifth embodiment of the present invention will be described. FIG. 24 relates to the fifth embodiment of the present invention and is a perspective view showing a relationship between a protective body and a capsule endoscope body. Note that structure that has the same operation and effect as that in each of the above described embodiments is given the same symbol and a description thereof is omitted.

In each of the above described embodiments, the protective body is formed in a bag shape, however, in the fifth embodiment, a protective body is employed in a form that covers the entire area of the capsule endoscope body without being formed in a bag shape. The capsule endoscope 2-4 of the fifth embodiment covers the entire capsule endoscope 2a using a protective body formed by bonding two members in a top/bottom direction or in a left/right direction. In FIG. 24, a protective body 50 is shown that is formed by two members that are separated into top and bottom portions, namely, into a lid body 51 and a bottom body 52.

A transparent plate 53 is provided at a position on the bottom body 52 facing lens cover 12 and the LED covers 13. In addition, adhesive layers 56 are provided on a frame portion 54 of the lid body 51 and on a frame portion 55 of the bottom body 52 that adhere these two together. Note that the protective body 50 is also formed by a member having elasticity in the same way as each of the above embodiments.

As is shown in FIG. 24, in the protective body 50 of the fifth embodiment, after the orientations of the lid body 51 and the bottom body 52 have been matched relative to the capsule endoscope body 2a such that the transparent plate 53 is on the lens cover 12 side. The capsule endoscope body 2a is then totally covered by covering the capsule endoscope body 2a with the lid body 51 from above while fitting the bottom body 52 from below, and then adhering the respective frame portions 54 and 55 together using the respective adhesive layers 56 of each.

As a result, it is possible to protect the entirety of the capsule endoscope body 2a using the protective body 50, and it is possible to prevent damage occurring during an impact to the capsule endoscope body 2a. In this case, because the protective body 50 is an elastic body, it can be used for an unlimited number of times provided that cuts or cracks do not occur. If cuts or cracks do occur, it is sufficient if the protective body 50 is cut open at that portion and the capsule endoscope body 2a is removed therefrom, and a new protective body 50 attached.

Note that the bonding of the lid body 51 to the bottom body 52 is not limited to being achieved by adhesion and they may be engaged together by providing protrusions and grooves in the two, or by pressure insertion using concave and convex portions.

Figure 25:
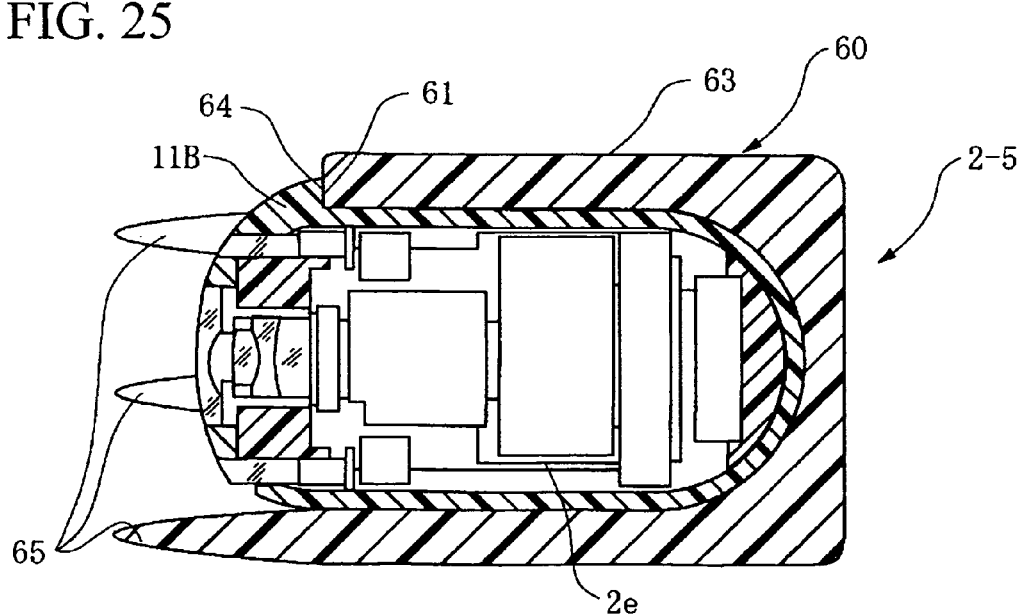
FIG. 25 is a structural view of a capsule endoscope according to a sixth embodiment of the present invention.
Figure 26:
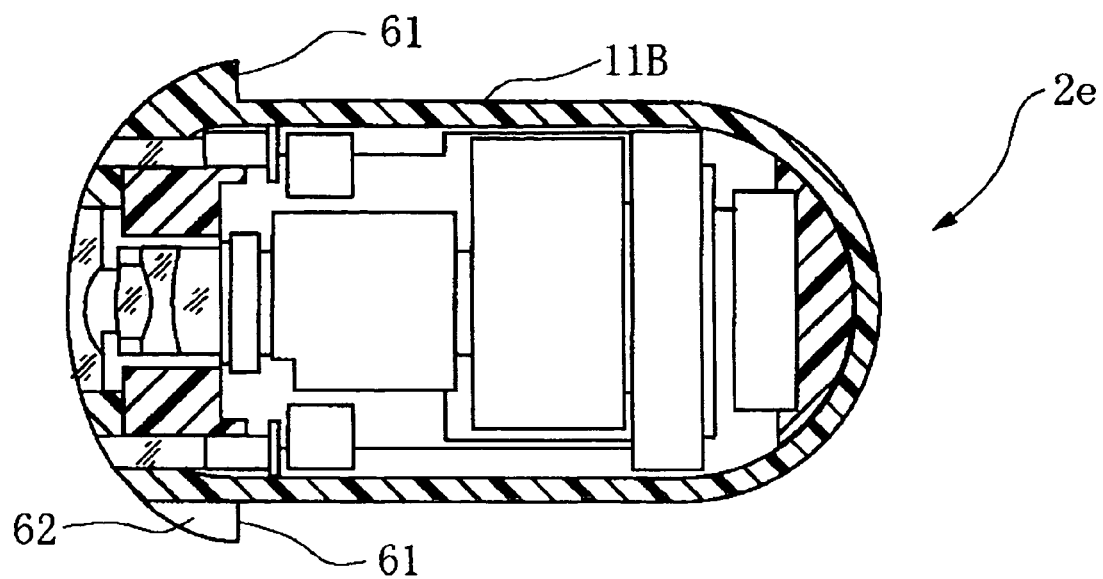
FIG. 26 is an explanatory view showing a capsule endoscope body according to a sixth embodiment of the present invention.
Figure 27:
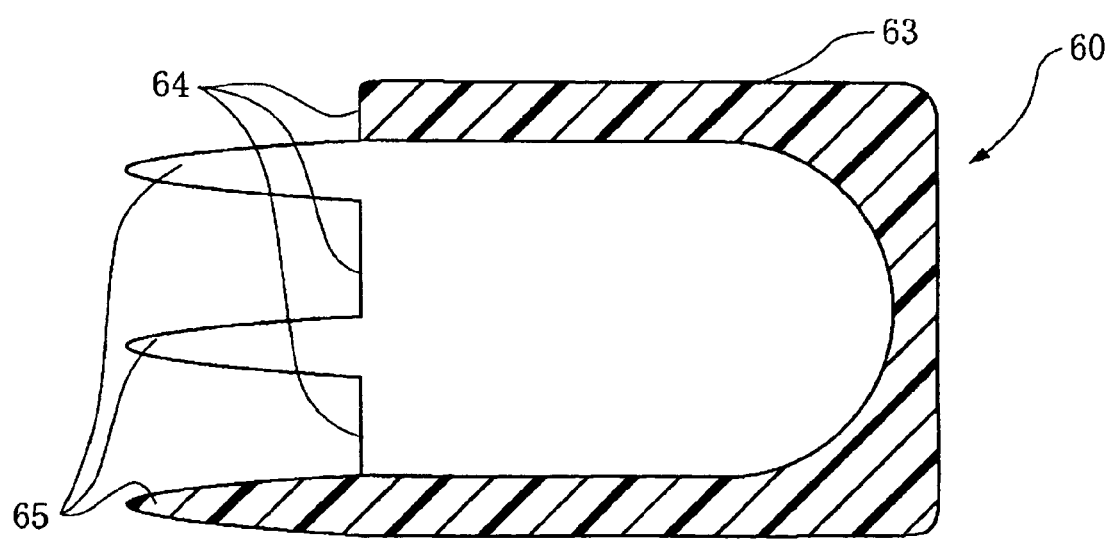
FIG. 27 is an explanatory view showing a protective body according to a sixth embodiment of the present invention.

Next, the sixth embodiment of the present invention will be described. FIGS. 25 to 27 relate to the sixth embodiment of the present invention. FIG. 25 is a structural view of a capsule endoscope. FIG. 26 is an explanatory view showing a capsule endoscope body. FIG. 27 is an explanatory view showing a protective body. Note that structure that has the same operation and effect as that in each of the above described embodiments is given the same symbol and a description thereof is omitted.

As is shown in FIGS. 25 to 27, in the capsule endoscope 2-5 of the sixth embodiment an umbrella shaped step portion 61 is provided at a distal end side thereof, and a protective body 60 that is provided with a plurality of protrusions 65 is packaged around a capsule endoscope body 2e that has a case 11B that is formed by cutting a plurality of notch portions 62 in the step portion 61. Other than the fact that the case 11B is different, the remainder of the structure of the capsule endoscope body 2e is fundamentally the same as that of the above described capsule endoscope body 2a.

At a distal end side of a trunk portion 63 that covers the case 11B of the capsule endoscope 2e the protective body 60 is provided with an abutting portion 64 that performs positioning by abutting against the step portion 61 of the case 11B, and a plurality of protrusions 65 that protrude forwards through the notch portions 62 of the case 11B.

In the capsule endoscope 2-5 of the sixth embodiment as well, when the capsule endoscope 2-5 collides against an object, the protrusions 65 or portions other than the protrusions 65 of the protective body 60 are deformed, and the shock is absorbed in the same way as in each of the above described embodiments.

Note that, in each of the above described embodiments, a description is given of when the protective bodies 30 (30A and 30B), 35 (35A), 40, 45, 50, and 60 are formed by soft members having elasticity, however, it is also possible for the protective bodies to be formed not by soft members, but from a hard resin that absorbs shock by breaking or disintegrating such as, for example, polymethyl methacrylate (PMMA), acrylonitrile butadiene styrene (ABS), polycarbonate (PC) or the like.

Moreover, because it is possible to recover the capsule endoscope body 2a (or 2b to 2e) without it becoming damaged, images observed by the capsule endoscope body 2a (or 2b to 2e) may be accumulated as data inside the capsule endoscope body 2a (or 2b to 2e), without being transmitted by radio from the capsule endoscope body 2a (or 2b to 2e) to the apparatus body 3, and this image data may be recovered after the capsule endoscope body 2a (or 2b to 2e) has been recovered. As a result of this, it is possible to omit the radio circuit portion 23 and the effect is obtained that the overall capsule endoscope is reduced in size.

As has been described above, according to the present invention, by providing a protective body that packages the exterior of a capsule endoscope body without obstructing the field of vision thereof, it is possible to protect the capsule endoscope body from shocks caused by collisions with surrounding objects.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

What is claimed is:

1. A capsule endoscope that is insertable into an object being examined and for making observations of an interior of the object being examined, the capsule endoscope comprising:

a capsule endoscope body including a transmitter for wirelessly transmitting observation images;

a protective body that is provided on an exterior of the capsule endoscope body to protect the capsule endoscope body while the capsule endoscope is making the observations, the protective body having an open portion to receive the capsule endoscope body and to protrude more than the capsule endoscope body without obstructing a field of vision of the capsule endoscope body while it is in use, and that protects the capsule endoscope body from shocks caused by collisions with surrounding objects while it is in use, and without obstructing the transmission of the observation images;

a shock sensor for sensing a shock on the protective body; and a control section which records a shock threshold value of the shock sensor and a counter limit value, wherein the control section counts the number of shocks on the protective body and when a count value of the shock sensor exceeds the count limit value, the control section sends a command to display a caution urging a replacement of the protective body on a monitor.

2. A capsule endoscope according to claim 1, wherein the protective body is formed by an elastic body.

3. A capsule endoscope according to claim 1, wherein the protective body is formed by a solid body that is freely plastically deformable.

4. A capsule endoscope according to claim 1, wherein the protective body comprises a transparent portion.

5. A capsule endoscope that is insertable into an object being examined and for making observations of an interior of the object being examined, the capsule endoscope comprising:

a capsule endoscope body including a transmitter for wirelessly transmitting observation images;

a protective body that is provided on an exterior of the capsule endoscope body to protect the capsule endoscope body while the capsule endoscope is making the observations, the protective body having an open portion to receive the capsule endoscope body and to protrude more than the capsule endoscope body without obstructing a field of vision of the capsule endoscope body while it is in use, and that protects the capsule endoscope body from shocks caused by collisions with surrounding objects while it is in use, and without obstructing the transmission of the observation images;

a shock sensor for sensing a shock on the protective body, a control section which records a shock threshold value of the shock sensor and a counter limit value; and a monitor; wherein the control section counts the number of shocks on the protective body, and when a count value of the shock sensor exceeds the count limit value, the control section makes the monitor display a caution urging a replacement of the protective body.

* * * * *